(12) United States Patent
Weiss

(10) Patent No.: US 11,911,547 B2
(45) Date of Patent: Feb. 27, 2024

(54) APPARATUS AND METHOD FOR MANUFACTURING READY-TO-USE SOLUTIONS FOR PERITONEAL DIALYSIS

(71) Applicant: FRESENIUS MEDICAL CARE DEUTSCHLAND GMBH, Bad Homburg (DE)

(72) Inventor: Stefan Weiss, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/477,105

(22) PCT Filed: Jan. 11, 2018

(86) PCT No.: PCT/EP2018/050673
§ 371 (c)(1),
(2) Date: Jul. 10, 2019

(87) PCT Pub. No.: WO2018/130617
PCT Pub. Date: Jul. 19, 2018

(65) Prior Publication Data
US 2019/0351122 A1 Nov. 21, 2019

(30) Foreign Application Priority Data

Jan. 11, 2017 (DE) .................... 10 2017 000 194.4
Jan. 20, 2017 (DE) .................... 10 2017 000 533.8

(51) Int. Cl.
*A61M 1/28* (2006.01)
*A61M 1/16* (2006.01)
(Continued)

(52) U.S. Cl.
CPC .............. *A61M 1/28* (2013.01); *A61J 1/1431* (2015.05); *A61M 1/166* (2014.02);
(Continued)

(58) Field of Classification Search
CPC .. A61M 1/1686; A61M 1/166; A61M 1/1668; A61M 1/28; A61M 1/1656; A61M 1/168; A61L 2/04
See application file for complete search history.

(56) References Cited

U.S. PATENT DOCUMENTS 6,663,829 B1 * 12/2003 Kjellstrand ........... A61J 1/2093
422/1
7,694,814 B1 * 4/2010 Cristobal ............. A61B 8/4422
206/438

(Continued)

FOREIGN PATENT DOCUMENTS

DE    19825568    12/1999
DE    60030277    8/2007
(Continued)

OTHER PUBLICATIONS

Chipperfield, Welding and Joining Techniques for polymeric medical devices, TWI Global, 2001, https://www.twi-global.com/technical-knowledge/published-papers/welding-and-joining-techniques-for-polymeric-medical-devices-may-2001, accessed Dec. 18, 2020 (Year: 2001).*

(Continued)

*Primary Examiner* — Bradley R Spies
*Assistant Examiner* — Jeannie McDermott
(74) *Attorney, Agent, or Firm* — Jacobson Holman PLLC

(57) ABSTRACT

The invention relates to an apparatus for preparing ready-to-use solutions for peritoneal dialysis that has a sterilization compartment; a filling line leading to the sterilization compartment and having a connector arranged at its end at the compartment side for connecting a disposable; a water treatment system arranged in the filling line; and a sealing system. The invention further relates to a disposable for preparing ready-to-use solutions for peritoneal dialysis in (Continued)

such an apparatus and to a method of preparing ready-to-use solutions for peritoneal dialysis using such an apparatus and such a disposable.

5 Claims, 1 Drawing Sheet

(51) Int. Cl.
*A61J 1/14* (2023.01)
*A61L 2/04* (2006.01)
*A61J 1/05* (2006.01)
*A61L 2/10* (2006.01)

(52) U.S. Cl.
CPC ........ *A61M 1/1668* (2014.02); *A61M 1/1672* (2014.02); *A61M 1/1674* (2014.02); *A61M 1/1686* (2013.01); *A61J 1/05* (2013.01); *A61L 2/04* (2013.01); *A61L 2/10* (2013.01)

(56) References Cited

U.S. PATENT DOCUMENTS

| | | | | |
|---|---|---|---|---|
| 2003/0105435 | A1* | 6/2003 | Taylor | A61M 1/1666 604/252 |
| 2012/0310150 | A1* | 12/2012 | Brandl | A61M 1/1666 604/410 |
| 2013/0228505 | A1* | 9/2013 | Burbank | A61J 1/05 210/257.2 |
| 2017/0281845 | A1* | 10/2017 | Manda | A61K 31/716 |
| 2017/0319770 | A1* | 11/2017 | Fitzgerald | A61M 1/284 |
| 2018/0369470 | A1* | 12/2018 | Garvey | A61M 1/287 |

FOREIGN PATENT DOCUMENTS

| | | | |
|---|---|---|---|
| GB | 2091126 | 7/1982 | |
| WO | 97/05851 | 2/1997 | |
| WO | 97/41902 | 11/1997 | |
| WO | WO 99/62573 | 12/1999 | |
| WO | WO 00/57833 | 10/2000 | |
| WO | WO00/57935 | 10/2000 | |
| WO | 2012/129501 | 9/2012 | |
| WO | WO 2013/055283 | 4/2013 | |
| WO | WO-2013141896 A1 * | 9/2013 | .......... A61M 1/1656 |

OTHER PUBLICATIONS

Gen, Thermal Welding for Sterile Connections, Genetic Engineering and Biotechnology News, Thermal Welding for Sterile Connections Apr. 1, 2006, vol. 26, No. 7, https://www.genengnews.com/magazine/47/thermal-welding-for-sterile-connections/ Accessed Dec. 17, 2020. (Year: 2006).*

* cited by examiner

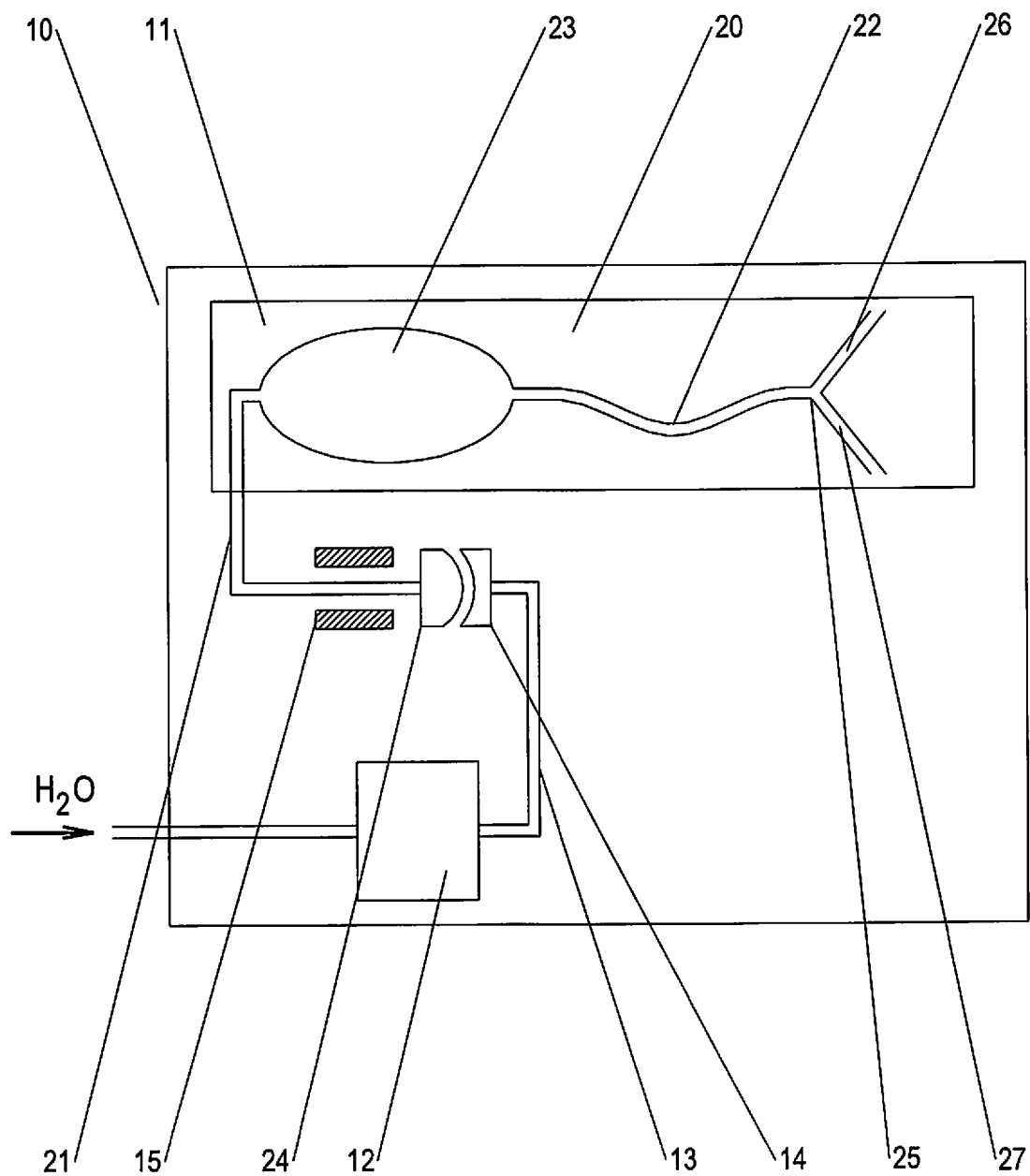

APPARATUS AND METHOD FOR MANUFACTURING READY-TO-USE SOLUTIONS FOR PERITONEAL DIALYSIS

The invention relates to an apparatus, to a disposable, to a method, and to a system for manufacturing ready-to-use solutions for peritoneal dialysis.

Solutions for peritoneal dialysis are frequently prepared on an industrial scale in the prior art and are provided to the patient ready to use. It is furthermore known to provide multi-chamber bags having the individual components of such solutions to be able to mix the individual components on site. In both cases, the unit provided comprises all the ingredients of the ready-to-use solution, with water being a main component thereof.

It is disadvantageous about these forms of provision that the shipping and storing of ready-to-use solutions or of multi-chamber bags having all the individual components of such solutions are complex and/or expensive. It was contemplated in WO 2013/055283 A1 only to provide the patient with concentrates and to prepare the ready-to-use solution at the site of application by adding mains water. Provision is made to be able to make use of sterile water at the application site when mains water is treated with a reverse osmosis system prior to the mixing with the concentrate and that the prepared ready-to-use solution passes through a sterile filter before application.

It is the object of the invention to prepare ready-to-use solutions composed only of concentrates at the application site in which a sterility of the solution is secured to a greater degree than in the known solutions.

Against this background, the invention relates to an apparatus for manufacturing ready-to-use solutions for peritoneal dialysis that has a sterilization compartment; a filling line leading to the sterilization compartment and having a connector arranged at its end at the compartment side; a water treatment system arranged in the filling line; and a sealing system.

A disposable or at least a solution bag of a disposable can be introduced into the sterilization compartment in the operation of such an apparatus. The connector can, for example, be configured such that a reversibly releasable mechanical connection to a suitable mating connector at a disposable can take place. It can comprise a male or a female interface, a latching nose or a latching receiver, an external thread or an internal thread or the like. The connector can be configured as a Luer connection.

The apparatus has an access opening through which a disposable can be placed into the sterilization compartment. A termination element such as a cover flap is preferably present by which the access opening can be closed.

Provision is made in an embodiment that the sterilization compartment is a heating compartment and preferably an autoclave. In the case of a heating compartment, the apparatus comprises an associated heating and is configured such that a temperature of 60° C. to 160°, preferably of 80° C. to 120° C., can be set in the heating compartment. When an autoclave is used, a solution that is in a container that is received in the heating compartment can be heated at an elevated pressure. The heating can take place isochorically or additional pressure beyond this can even be built up. An outgassing is thus avoided in the case of a carbonate-buffered solution, for example. Higher temperatures can furthermore be reached before the boiling point of the solution is reached.

In an embodiment, the apparatus comprises a radiation source with which a disposable located in the sterilization compartment can be irradiated. A radiation source can be present in addition to or instead of a heating. The radiation source can be a source for UV light.

Provision is made in an embodiment that the sealing system has a heatable sealing bar and/or an ultrasound generator. Sealing systems having heatable sealing bars are known, for example, from film welding devices and evacuating devices. An inflow line formed as a plastic hose of a disposable located in the chamber can be closed using such a system. Ultrasonic welding can also be suitable to be able, for example, to weld an inflow line comprising a plastic hose of a bag.

Provision is made in an embodiment that the filling line has an interface at its oppositely disposed side accessible for the user for connection to a water supply.

Provision is made in an embodiment that the water treatment plant has at least one filter, preferably a reverse osmosis unit. In addition, the water treatment plant can also include adsorptive elements and sterile filters. The plant can also have stills.

Against the initially named background, the invention furthermore relates to a disposable for preparing ready-to-use solutions for peritoneal dialysis in an apparatus in accordance with the invention, wherein the disposable has a container having at least one chamber for receiving water, and wherein the disposable has an inflow line leading into the chamber that comprises a mating connector for a releasable connection to the connector of the apparatus. The mating connector can be configured, for example, such that a reversibly releasable mechanical connection to the connector of the apparatus can take place. It can comprise a female or a male interface, a latching receiver or a latching nose, an internal thread or an external thread or the like.

Provision is made in an embodiment that the container includes a solid or liquid concentrate for a peritoneal dialysis solution in the same chamber or in a further chamber. The container can, for example, be a container having a plurality of chambers such as a multi-chamber bag, with two chambers being separated from one another by a weld seam and being able to be opened by exertion of pressure on one of the contacting chambers. It can, for example, be a two-chamber bag or a three-chamber bag, with one chamber being connected to the inflow line and being able to be filled with water, and with the other chamber or the other chambers including the solution concentrate or respective portions of the solution concentrate.

Provision is made in an embodiment that the disposable furthermore has a tubing set for connecting the container to a patient, with the tubing set and the container preferably being inseparably connected to one another. The tubing set can, for example, be produced in one piece with the container. The disposable can be produced entirely from plastic. The inflow line can be a plastic hose. The plastic material is preferably thermoplastic so that is can be thermally welded. Unlike the currently used disposables, the container is therefore a component of the closed system and no longer has to be connected to a tubing set.

The invention furthermore relates to a method of preparing ready-to-use solutions for peritoneal dialysis, wherein a disposable in accordance with the invention is placed into the sterilization compartment of an apparatus in accordance with the invention, wherein the connector of the apparatus is connected to the mating connector of the disposable, wherein the chamber of the disposable is filled with water through the filling line of the apparatus and the inflow line of the disposable, wherein the inflow line of the disposable is sealed using the sealing system of the apparatus, and wherein the filled disposable is sterilized by increasing the temperature in the sterilization compartment.

The sterilization can take place, for example, by heat and/or by irradiation. A heat sterilization can take place, for example, at a temperature of 60° C. to 150° C., preferably pf 80° C. to 120° C. It can be carried out at an elevated pressure of, for example, greater than 1.2 bar or greater than 1.5 bar. The temperature and pressure can be maintained, for example, for a time period of more than 10 minutes or more than 20 minutes to achieve a uniform temperature setting of the entire solution.

The inflow line of the disposable, which can, for example, be a plastic hose, can be sealed, for example, by thermal welding and/or ultrasonic welding such that fluid can no longer exit or enter into the chamber of the disposable during the sterilization. The disposable that has been welded closed forms a closed system that is substantially gas-tight and liquid-tight.

The apparatus has to be connected to a water line, for example to a normal drinking water line of a household, before the filling of the chamber of the container with water. This connection preferably already takes place before the insertion of the disposable or at least before the connection of the connector of the apparatus to the mating connector of the disposable such that the filling line is flushed with water and can thus be degassed.

On running through the filling line, the water is filtered in the water treatment plant and is preferably deionized and/or pre-sterilized. A reverse osmosis can be carried out in this respect. It is furthermore possible that an irradiation takes place and/or that a sterile filter is passed through.

The inflow line can therefore be welded closed after the filling with mains water and a closed system can thus be established. The system thus established is sterilized, and preferably heat sterilized, at the application site in the sterilization chamber which can be an autoclave.

Provision is therefore made within the framework of the method in accordance with the invention to prepare peritoneal dialysis solutions batch-wise at the application site. A ready-to-use peritoneal dialysis solution is mixed in a disposable at the application site, said disposable preferably being a prefabricated administration kit comprising a container and hoses so that the ready-to-use solution is present in a container. Alternatively, a plurality of solutions can also be presented separately in a multi-chamber bag system that are only mixed to form the ready-to-use solution before use. The filling and the mixing of the solution can in this respect take place with mains water, on the one hand, and from concentrate containers, on the other hand. However, it is preferred that the concentrates are already presented in liquid form or in dry form in the solution bag. The presented concentrates can optionally be presented in a different chamber, e.g. in a multi-chamber bag having a peel seam such as is disclosed in WO 2011/073274 A1.

Provision is made in an embodiment to analyze the solution prepared in the disposable within the framework of the method in accordance with the invention before the application at a patient, for example by means of a conductivity measurement and/or a pH measurement. It can be ensured in this manner that a concentrate having the correct amount of water has been diluted and thus a solution to be dispensed having the correct concentration has been prepared.

The invention finally relates to a system comprising an apparatus in accordance with the invention and a disposable in accordance with the invention placed into the sterilization compartment of said apparatus, wherein the connector of the apparatus is connected to the mating connector of the disposable.

Further details and advantages of the invention result from the following embodiment described with reference to the FIGURE.

The FIGURE shows a schematic representation of an apparatus 10 in accordance with the invention having a disposable 20 in accordance with the invention received therein that is configured as a bag and hose system.

The apparatus 10 comprises an autoclave 11 in which the disposable 20 is arranged. The apparatus furthermore comprises a water treatment system 12 that includes a reverse osmosis unit and comprises a filling line 13 that runs from a water source located outside the apparatus 10 up to a connector 14 in or close to the autoclave 11. The connector 14 serves the connection of the filling line 13 to the disposable 20. The treatment system 12 is located at the filling line 13 so that water has to run through the water treatment system 12 on the way from the water source to the connector 14. A sealing system 15 having two heating bars for welding an inflow line 21 of the disposable 20 and for establishing a closed system within the disposable 20 is located upstream of the connector 14. The connector 14 and the sealing system 15 can be arranged either in the autoclave 11 or next to the autoclave 11. The sealing system is preferably arranged within the sterilization compartment. All the components of the closed system are disposed within the sterilization compartment in this manner.

The disposable 20 comprises, beside the inflow line 21, a tubing set 22 and a container 23 connected to the inflow line 21 and the tubing set 22. This disposable 20 offers a cost saving in comparison with conventional disposables due to the prefabricated connection of the tubing set 22 and the container 23 since otherwise necessary separate connectors are dispensed with. The inflow line 21 has at its end remote from the container 23 a mating connector 24 that is releasably mechanically connected to the connector 14 of the apparatus. The tubing set 22 comprises a Y junction 25 having a line 26 for connection to a PD catheter and having a further line 27 for draining consumed concentrate. The line 27 can be connected in a fluid-tight manner to a container, preferably to a bag, for receiving the consumed dialyzate.

The line 22, the junction 25, and the lines 26 and 27 are likewise located within the apparatus 10 or within the sterilization compartment, as can be seen from the FIGURE.

The filling volume of the container 23 amounts, for example, to two to five liters, as is customary in the prior art. Because the disposable 20 can be filled at the application site and because a transport can thus be omitted, it is, however, also conceivable to use instead of a plurality of solution bags having two to five liters content a substantially larger container having a filling volume of, for example, up to thirty liters. A smaller last bag can be used in the therapy in addition to such a large solution bag.

A dialysis concentrate can be presented in the container. The concentrate is preferably presented in a chamber of the bag, wherein the chamber can be emptied into the main chamber of the container through a breakable closure. The breakable closure can be a peel seam.

The disposable furthermore preferably includes a breakable closure before or in the drain line 22. The closure can, for example, be configured as a safety peel seam that defines a run-out chamber or as a breaking cone in the drain line. It can be ensured in this manner that a complete mixing of the concentrate with the water takes place before the solution bag is administered to the patient.

In use, the disposable 20 is placed into the autoclave 11 and the inflow line 21 of the disposable is connected to the filling line 13 of the apparatus 10. More precisely, the connector 14 is connected to the mating connector 24. The connection of connector 14 and mating connector 24 preferably takes place in the interior of the apparatus, with the connector 14 being able to be accessible to the user, for example, through the open autoclave 11. On the connection, the inflow line 21 of the disposable is simultaneously inserted between the heating bars of the sealing system 15.

The device carries out the filling of the container 23, the welding of the inflow line 21 and the heating and pressurization in the autoclave 11 for the heat sterilization in an automated manner according to the user input. The disposable 20 can thus be inserted and the process started in the evening, for example, and the disposable 20 can be removed with a ready-to-use peritoneal dialysis solution the next morning.

After the heat sterilization and before use, the solution must first reach a temperature ready for use. To achieve this on a sterilization overnight, provision can be made that the apparatus ventilates the autoclave 11 with environmental air in an automated manner after the heat sterilization to achieve a cooling.

The method described is suitable for preparing solutions both for continuous ambulatory peritoneal dialysis (CAPD) and for automated peritoneal dialysis (APD).

The disposable 20 can, for example, be removed from the autoclave 11 and can be utilized in a known manner in an APD device for ADP operation. The apparatus can alternatively have an additional line that can be directly connected to an APD device. In such a case, the disposable 20 does not have to be removed from the autoclave 11 for the therapy, but the dialysis solution can rather be fed directly from the filled disposable 20 still present in the autoclave 11 to the APD device. In this respect, the autoclave 11 can also be used as a heating for the temperature adjustment of the dialysis solution in the therapy so that a heating no longer has to be present in the actual APD device.

Provision can also be made in a variant that an APD device is integrated in the apparatus 11, for example a gravimetric APD device. In such a case, the heating of the solution during the therapy could also take place by the autoclave 11 and the autoclave 11 can be installed at such a height that a gravimetric APD is made possible. A raising of the filled container 23 to a level required for the gravimetric APD would be superfluous since the filling would take place on site.

The invention claimed is:

1. An apparatus for preparing ready-to-use solutions for peritoneal dialysis, the apparatus comprising:
   a sterilization compartment selected from the group consisting of an autoclave, an irradiation compartment, and a combination thereof;
   a filling line leading to the sterilization compartment;
   a connector having a compartment-side end for connecting an inflow line of a disposable;
   a water treatment system arranged in the filling line; and
   a sealing system;
   characterized in that the inflow line of the disposable is sealed closed using the sealing system, the sealing system and the connector for connecting a disposable are arranged within the sterilization compartment, and the water treatment system is arranged outside the sterilization compartment, wherein the disposable comprises a container having at least one chamber for receiving water and a tubing set for connecting the container to a patient, wherein the disposable is a prefabricated administration kit formed by the container inseparably connected to the tubing set, and wherein the apparatus integrates into an automated peritoneal dialysis (APD) device.

2. An apparatus in accordance with claim 1, characterized in that the irradiation compartment has a radiation source that emits UV light.

3. An apparatus in accordance with claim 1, characterized in that the sealing system has a heatable sealing bar and/or an ultrasound generator.

4. An apparatus in accordance with claim 1, characterized in that the filling line has an oppositely disposed end accessible to the user for connection to a water supply.

5. An apparatus in accordance with claim 1, characterized in that the water treatment system comprises a reverse osmosis unit and/or a sterile filter.

* * * * *